(12) United States Patent
Thaller et al.

(10) Patent No.: US 7,807,395 B2
(45) Date of Patent: Oct. 5, 2010

(54) METHOD FOR THE DETERMINATION OF PROSTHETIC INFECTIONS

(75) Inventors: Maria Cristina Thaller, Milan (IT); Gianmaria Rossolini, Milan (IT); Laura Selan, Milan (IT); Claudio Passariello, Milan (IT)

(73) Assignee: BRACCO S.p.A., Milan (IT)

( * ) Notice: Subject to any disclaimer, the term of this patent is extended or adjusted under 35 U.S.C. 154(b) by 205 days.

(21) Appl. No.: 10/135,827

(22) Filed: May 1, 2002

(65) Prior Publication Data

US 2002/0197280 A1 Dec. 26, 2002

(51) Int. Cl.
*G01N 33/554* (2006.01)
*A61K 39/085* (2006.01)

(52) U.S. Cl. .................. 435/7.32; 424/243.1

(58) Field of Classification Search ............ 435/2, 435/7.1, 7.33, 36; 424/9.2
See application file for complete search history.

(56) References Cited

U.S. PATENT DOCUMENTS 5,366,505 A 11/1994 Farber

FOREIGN PATENT DOCUMENTS

| GB | 992 132 A | 5/1965 |
| WO | WO 90 03398 A | 4/1990 |
| WO | WO 91 03572 A | 3/1991 |
| WO | WO 96 09321 A | 3/1996 |

OTHER PUBLICATIONS

Singer et al.(Abstract No. R2261, 19th European Congress of Clinical Microbiology and Infectious Diseases, Helsinki, Finland, May 16, 2009).*
Karamanos et al, "The major 20 kDa polysaccharide of *Staphylococcus epidermidis* extracellular slime and its antibodies as powerful agents for detecting antibodies in blood serum and differentiating among slime-positive and -negative S. epidermidis and other *staphylococci* species", *Arch. Biochem. Biophys.*, 1997, pp. 389-395.
Sanford et al, "Lectin-biotin assay for slime present in in situ biofilm produced by *Staphylococcus epidermidis* using transmission electron microscopy (TEM)", *Journal of Industrial Microbiology*, 1995, vol. 15, No. 3, pp. 156-161.
Hussain et al, "The slime of coagulase-negative *staphylococci*: Biochemistry and relation to adherence", FEMS Microbiology Reviews 104 (1993) 191-208.
Selan et al, "Immunodiagnosis of late-onset vascular graft infections by measurement of serum antibodies to *staphylococcal* slime polysaccharide antigens", draft paper.
Selan et al, "Diagnosis of vascular graft infections with antibodies against *staphylococcal* slime antigens", The Lancet, vol. 359, Jun. 22, 2002, pp. 2166-2168.
Costerton et al, "Bacterial Biofilms: A Common Cause of Persistent Infections", Science, May 21,1999, vol. 284, pp. 1318-1322.

* cited by examiner

*Primary Examiner*—Robert A Zeman
(74) *Attorney, Agent, or Firm*—Nixon & Vanderhye P.C.

(57) ABSTRACT

A method for the laboratory determination of prosthetic infections is described. This method, performed on biological fluids isolated from patients, is based on the detection of antibodies specific for the polysaccharides produced by bacteria colonizing prosthetic devices.

2 Claims, No Drawings

METHOD FOR THE DETERMINATION OF PROSTHETIC INFECTIONS

The present invention refers to a method for the determination of prosthetic infections in which at least one *Staphylococcus* strain is involved. The method is based on the detection of antibodies reacting with a slime polysaccharide produced by virulent staphylococcal strains, from blood samples or other biological fluid samples.

The invention also provides a process for preparing a polysaccharide to use in the above method, starting from cultures of virulent staphylococcal strains, as well as the polysaccharide itself which is obtained by the cited process.

Prosthetic infections represent a severe problem in general surgery, cardiovascular surgery, orthopedics, ophtalmology and odontology, all sectors in which the introduction of biomaterials has become routinary. Prosthetic devices are also widely used in oncology for artificial nutrition and chemotherapy.

The most significant aspects of prosthetic infections are the following:
 their incidence is generally reported to be 2 to 6% of the cases, following the first introduction of the biomaterial;
 when a biomaterial is substituted by a new one, as a consequence of an infection, the incidence of re-infections is about 60%;
 infections may cause functional loss of organs or their parts or even death of the patient in 25 to 45% of the cases, although in some particular cases, as for cardiac surgery, mortality is much higher and in some fields of medicine, as for example odontology, no mortality is usually associated with prosthetic infections;
 hospitalization of patients is frequently very long and expensive;
 diagnosis of these infections is difficult for the almost complete absence of specific clinical signs;
 the greatest part of these infections (over 85%) is caused by coagulase negative staphylococci (and to a lesser extent by coagulase positive staphylococci), although other microorganisms, as enteric bacteria, pseudomonads and enterococci, can also be isolated in various cases (frequently in association with at least one staphylococcal strain).

While causing these infections bacteria are strongly glued to the surface of biomaterials, forming colonies that evolve with time in biofilms that may almost entirely cover the surface of the biomaterial, biasing its tissue integration.

Following adhesion bacteria undergo important metabolic modifications, reducing their replicative rate, though maintaining a high biosynthetic activity. The main products of this activity are extracellular polysaccharides (generally indicated as slime) that form a thick and dense fibrous layer protecting bacterial cells from chemicals, radiations, phagocytes, and antibodies.

Slime-embedded bacteria, growing on biomaterials, when exposed to antibiotics, exhibit minimal inhibitory and minimal bactericidal concentrations that can be even hundreds of times higher than the corresponding values obtained when bacteria are grown in the absence of the biomaterial.

When a biofilm reaches a determined critical mass, it releases in the surrounding liquid environment little aggregates of bacterial cells that may move to colonize new surfaces of the biomaterial.

Prosthetic infections are frequently characterized by scarce and non specific clinical signs, that are most often confused with minor viral episodes, and that disappear following common antibiotic therapy to manifest again after some time. These episodes are generally due to the release of small bacterial aggregates from the biofilm, that while circulating in blood are easily recognized by the immune defenses of the host, causing fever, and that, being in the planktonic form, are easily killed by common antibiotics, thus mimicking the eradication of the infection. Clinical signs become evident in the advanced phases of the infection, with formation of large tumefactions of the soft tissues surrounding the graft, or fistulas, or evident signs of general compromission.

Due to this peculiar characteristics early diagnosis is extremely difficult, even as a consequence of the high incidence of false negatives following cultural microbiological analyses, depending on the fact that sessile bacteria are not able to rapidly adapt to in vitro cultural conditions.

Till now diagnosis of vascular graft infections has been based on the analysis of objective clinical parameters, blood parameters, and instrumental data obtained by ultrasonography, computed tomography, magnetic resonance, esophagogastro-duodenoscopy, and scintigraphy following injection with radio-labelled leukocytes. This way it is in most cases not possible to reveal the early phases of infection for the insufficient sensitivity or for the lack of well defined criteria of interpretation of data and images.

Overall the actual diagnostic possibilities are absolutely inadequate, particularly in the early phases of the disease that are more favourable for a successful therapy.

It has now been found, and this is the object of the present invention, a reliable and unexpensive method, that can be easily applied to serum samples or other biological fluids, able to reveal the presence of infections involving prosthetic devices even in the early phases of development. This method can be routinely performed for the constant monitoring of patients that were treated with the introduction of any kind of prosthetic device and are at risk for infection, especially caused by staphylococci.

This method consists in the quantitative determination of the presence of antibodies, specifically directed against extracellular polysaccharides, extracted from virulent strains of staphylococci.

Furthermore, the present invention provides a method for preparing and purifying these extracellular polysaccharides from adequately grown staphylococcal cells.

Staphylococcal strains that may be used for this method are both coagulase-negative and positive, either virulent ones or anyway able to produce slime. In particular, virulent *Staphylococcus epidermidis* or *Staphylococcus aureus* strains are preferred.

These strains can be obtained either directly from patients suffering from a prosthetic infection or from standard culture collections of reference strains. The characteristics of such a typical strain are reported in the following Example 1. Experiments were also indicative when performed using the *Staphylococcus aureus* strain deposited by the applicant at DSMZ-Deutsche Sammlung Von Mikroorganismen Und Zellkulturen GmbH, Mascheroder Weg 1b, D-38124 Braunschweig, Germany on Jan. 22, 1998, which was assigned Accession No. DSM 11942.

Bacteria are grown in the liquid medium described in Hussain et al., J. Med. Microbiol. 34:143-147, 1991 (HHW medium), with some modifications as reported in the following Example 2.

The procedure to prepare the polysaccharides according to the invention essentially involves the following steps:
 a) culturing the staphylococcal strains in the modified HHW medium for a period of 4-6 days;
 b) homogenizing the bacterial cells in a physiological buffer c) centrifugating at 13,000×g for 15 minutes and separating the surnatant;
d) desalting by dyalisis the surnatant using membranes with a cut-off of 12 kDa;
e) freezing and lyophilizing the solution obtained in (d);
f) suspending the lyophilized material in a deproteinizing solution, for example tricloroacetic acid;
centrifugating at 30,000×g the solution obtained (f) and separating the surnatant with addition of ethanol;
h) centrifugating the surnatant of step (g) at 20,000×g to obtain the polysaccharide;
i) washing the precipitated polysaccharide with absolute ethanol, dehydrating in vacuo and suspending it in sterile $H_2O$.

Quantification of the purified polysaccharide could for example be performed according to the method described by Pelkonen et al., Journal of Bacteriology 170, 2646, 1988.

The polysaccharide obtained according to the above described method is used in the assay for the determination of antibodies in serum or other biological fluids from patients having a prosthetic device inserted.

Preferably the assay determines the presence of antibodies of the class IgG and/or IgM, following conventional immunochemical procedures, as for example enzyme linked immunosorbent assay (ELISA), gel immuno-precipitation, immuno-diffusion or counter-immuno-electrophoresis, radioimmunoassay, complement fixation, and passive haemoagglutination.

A solid phase method is preferred in which the polysaccharide is immobilized to a solid surface, as for example microtiter wells and then allowed to react with the sample, in conditions appropriate for the formation of the immune complex. Once the immune complex has formed it can be revealed by reaction with appropriate molecules, as for example antibodies or their immunocompetent fragments, labelled with radioactive isotopes, chemioluminescent or fluorogenic substances, or coupled to enzymes catalyzing colorimetric reactions and other similar substances.

The efficiency of the method disclosed by the invention was confirmed by the following experiments.

In a first set of experiments sera from 15 patients with a vascular graft infection were analyzed. The presence of a prosthetic infection in these patients was confirmed by microbiological analyses of both samples taken from the periprotesic tissues and of the grafts themselves after their surgical substitution. At least one staphylococcal strain was isolated from each sample.

Of these fifteen patients 11 showed overt clinical signs of infection while 4 had only non specific clinical signs of infection but were positive at scintigraphy after injection of $^{99m}$Tc-labelled leukocytes.

Sera from 10 adult, healthy subjects of both sex were used as negative controls.

Reactivity of the sera was assayed in an ELISA format, against:
a- monospecific biofilms formed by different staphylococcal strains (both clinical isolates and reference strains) formed on small polypropilene cylinders (0.5×1 mm);
b- polispecific biofilms formed by different staphylococcal strains (both clinical isolates and reference strains) formed on small polypropilene cylinders (0.5×1 mm);
c- surface proteins extracted from cultures of different staphylococcal strains.
d- the polysaccharides described in the present invention, extracted from cultures of *Staphylococcus aureus* DSM 11942 and of *Staphylococcus epidermidis* SA 1545 (see example 1 for characterization of this strain).

Experiments yielded the following results:
a-both IgG and IgM antibody titers against monospecific or polispecific staphylococcal biofilms or staphylococcal surface and secretory proteins were not significantly different in either infected and non infected patients;
b-both IgG and IgM antibody titers of against the staphylococcal polysaccharide of the invention were significantly different in infected and non infected patients; they moreover allowed to differentiate between overtly symptomatic infected patients and pauci-symptomatic, scintigraphy positive patients.

Table 1. Range, Mean and standard deviation of both IgG and IgM titers obtained in ELISA assays performed on serum samples of 11 patients with a symptomatic vascular graft infection, 4 patients with a pauci-symptomatic vascular graft infection but positive for scintigraphy after injection of $^{99m}$TC labelled leukocytes, and 10 healthy control subjects, using the polysaccharide extracted from cultures of *S. aureus* DSM 11942 to sensitize microtiter wells.

TABLE 1

| | DSM 11942 | | | | | |
|---|---|---|---|---|---|---|
| Patient Category (n.) | IgG 1/160 Range | IgG 1/160 Mean | IgG 1/160 SD* | IgM 1/160 Range | IgM 1/160 Mean | IgM 1/160 SD* |
| Infected Symptomatic (11) | 0.262-1.06 | 0.66 | 0.25 | 0.32-1.032 | 0.66 | 0.27 |
| Non Infected (10) | 0.177-0.266 | 0.17 | 0.03 | 0.101-0.195 | 0.14 | 0.04 |
| Infected pauci-symptomatic scintigraphy + (4) | 0.251-0.457 | 0.32 | 0.09 | 0.332-0.56 | 0.47 | 0.09 |

*Standard deviation

Table 2. Range, Mean and standard deviation of both IgG and IgM titers obtained in ELISA assays performed on serum samples of 11 patients with a symptomatic vascular graft infection, 4 patients with a pauci-symptomatic vascular graft infection but positive for scintigraphy after injection of $^{99m}$TC labelled leukocytes, and 10 healthy control subjects, using the polysaccharide extracted from cultures of *S. epidermidis* SA 1545 to sensitize microtiter wells.

TABLE 2

| Patient Category (n.) | IgG 1/160 Range | IgG 1/160 Mean | IgG 1/160 SD* | IgM 1/160 Range | IgM 1/160 Mean | IgM 1/160 SD* |
|---|---|---|---|---|---|---|
| | SA 1545 | | | | | |
| Infected symptomatic (11) | 0.173-0.971 | 0.47 | 0.21 | 0.31-1.071 | 0.56 | 0.2 |
| Non Infected (10) | 0.11-0.265 | 0.15 | 0.05 | 0.126-0.243 | 0.16 | 0.03 |
| Infected pauci-symptomatic scintigraphy + (4) | 0.202-0.445 | 0.29 | 0.11 | 0.287-0.483 | 0.37 | 0.06 |

*Standard deviation

In a second set of experiments a larger number of sera was assayed to determine both IgG and IgM titers in ELISA tests performed using only the polysaccharide of the invention to sensitize microtiter wells. All throughout these experiments the polysaccharide extracted from strain SA1545 (described in example 1) was used.

A total of 97 sera were tested in these experiments. Of these 97 sera, 19 were obtained from control patients not infected and not carrying a vascular graft, 3 were obtained from control patients not infected but carrying a vascular graft, 5 were obtained from patients carrying a vascular graft infected by Gram-negative bacteria, 13 were obtained from patients not infected but carrying a vascular graft and with a previous history of vascular graft infection caused by $Staphylococcus$ spp., and 57 were obtained from patients carrying a vascular graft infected by $Staphylococcus$ Spp.

Both IgG and IgM titers were determined in all these sera using 1/160 and 1/320 dilutions of the sera; two sets of duplicate determinations were performed to assess intra-experiment and inter-experiment reproducibility of the assay. ELISA assays were performed as described in example 4.

Results obtained in this second set of experiments are summarized in table 3.

Table 3. Results of Enzyme Linked Immunosorbent Assays (ELISA) performed using the polysaccharide preparation of $S.\ epidermidis$ SA1545 on 97 serum samples.

The IgM titres of each serum sample used for the statistical evaluation were mean values of four different determinations obtained in two different experiments. The IgG titres of each serum sample used for the statistical evaluation were mean values of two different determinations obtained in one experiment.

TABLE 3

| Patient category | Mean IgM titre (1:160) (range) | Mean IgM titre (1:320) (range) | Mean IgG titre (1:160) (range) | Mean IgG titre (1:320) (range) |
|---|---|---|---|---|
| A1) Control patients not infected and not carrying a vascular graft (n = 19) | 0.189 ± 0.037 (0.148 – 0.250) | 0.136 ± 0.024 (0.116 – 0.155) | 0,923 ± 0.18 (0.744 – 1.469) | 0.692 ± 0.21 (0.293 – 1.198) |
| A2) Control patients not infected but carrying a vascular graft (n = 3) | 0.153 ± 0.018 (0.134 – 0.167) | 0.111 ± 0.006 (0.105 – 0.116) | 1.083 ± 0.410 (0.706 – 1.585) | 0.823 ± 0.356 (0.476 – 1.243) |
| A) Total control patients not infected (n = 7) | 0.184 ± 0.037 (0.134 – 0.250) | 0.133 ± 0.024 (0.0.105 – 0.155) | 0,945 ± 0.22 (0.706 – 1.585) | 0.709 ± 0.23 (0.293 – 1.243) |
| B) Patients carrying a vascular graft infected by Gram-negative bacteria (n = 5) | 0.227 ± 0.063 (0.128 – 0.291) | 0.142 ± 0.038 (0.084 – 0.174) | 1.041 ± 0.265 (0.763 – 1.480) | 0.700 ± 0.259 (0.420 – 1.117) |
| C) Patients not infected but carrying a vascular graft and with a previous history of vascular graft infection caused by Staphylococcus spp. (n = 13) | 0.254 ± 0.076 (0.185 – 0.379) | 0.169 ± 0.055 (0.107 – 0.325) | 1.152 ± 0.424 (0.513 – 1.689) | 0.894 ± 0.527 (0.317 – 1.652) |
| D) Patients carrying a vascular graft infected by Staphylococcus spp. (n = 57) | 0.642 ± 0.516 (0.258 – >2.5) | 0.377 ± 0.396 (0.127 – 2.448) | 1.532 ± 0.278 (0.765 – 1.976) | 1.303 ± 0.332 (0.522 – 2.013) |

Results of Student T test for comparison of IgM titres measured at serum dilution=1:160:

$A(A1+A2)\ vs.\ D{:}p=1.7\times10^{-15}$.

$B\ vs.\ D{:}p=2.0\times10^{-4}$.

$C$ vs. $D: p=7.2\times10^{-8}$.

$A+B+C$ vs. $D: p=5.3\times10^{-23}$.

$A+C$ vs. $B: p=0.142$.

$A$ vs. $C: p=2.07\times10^{-11}$.

Results of Student T test for comparison of IgG titres measured at serum dilution 1:320:

$A(A1+A2)$ vs. $D: p=4.5\times10^{-21}$.

$B$ vs. $D: p=7.5\times10^{-8}$.

$C$ vs. $D: p=8.0\times10^{-7}$.

$A+B+C$ vs. $D: p=3.1\times10^{-21}$.

$A+C$ vs. $B: p=0.265$.

$A$ vs. $C: p=0.024$.

Comments:

The antibody titres detectable against the slime polysaccahride (SP) of *S. epidermidis* SA1545 showed significant differences in groups of different subjects, according to their clinical history.

Significantly higher antibody titres against the SA1545-SP were found in patients carrying vascular grafts infected by *Staphylococcus* spp., as compared to: i) control subjects with no history of such infection, either carrying a vascular graft or not; ii) patients carrying a vascular graft infected by Gram-negative bacteria; iii) subjects carrying a vascular graft not infected, but reporting a previous history of vascular graft infection by *Staphylococcus* spp. These data overall indicate that vascular graft infection caused by *Staphylococcus* spp. elicit a specific humoral immune response against the SP, and that this response can be detected by enzyme immunoassays using a solid phase sensitized with the SA1545 SP preparation, as described in the patent application.

Analysis of the isotypic response anti-SA1545 SP in the above groups of subjects showed significant differences of both IgM and IgG antibody titres. The IgM titres were most closely related with the state of active infection caused by *Staphylococcus* spp.

The existence of a statistically significant difference between titers of infected and non infected patients allows to establish a break point value over which it is possible to define a high probability of the existence of an infective process. It is moreover possible to use this method to monitor the patient after insertion of the graft, using the antibody titer measured at the time of implantation as a specific reference value in the follow up.

It appears clear that the above described method has several advantages, as compared to conventional diagnostic methods in this field, since it is easy to perform, inexpensive and allows to obtain reliable results (with no need of invasive procedures) even in the early phases of infection, when all the other available methods frequently fail to give clear diagnostic informations; this method moreover allows a periodic monitoring of patients for the occurrence of latent infections and could give reliable informations on therapeutic outcomes.

The invention finally provides a kit to perform the assay, which includes the polysaccharide preparation, standard antibodies and reagents for detection in adequate containers together with vehicles, excipients and additives like preservatives and stabilizers.

Preferably the kit will contain microtiter strips pre-sensitized with the antigen together with positive and negative control sera (with their original titres).

The following examples are intended to better clarify the invention.

EXAMPLE 1

Characterization of a Bacterial Strain Adequate for the Assay

A *Staphylococcus epidermidis* strain, indicated as SA1545—yielding the numeric code 6704773 when tested for identification with the API 20 STAPH identification system, was isolated from an aorto-bifemoral graft explanted from an adult male.

The isolate showed an evident dimorphism of colonies when grown on Columbia Agar plates supplemented with 5% defibrinated sheep blood. It was negative for mannitol fermentation when crown on mannitol salt agar, with colonies showing a 1 mm or less of diameter after 18 h of incubation at 37° C.

The isolate was sensitive to the following antibiotics, as assessed using the Kirby Bauer assay: Gentamycin, Vancomycin, Ofloxacin, Erytromycin, Imipenem, Cephalotin, Amoxicillin+clavulanic acid, cefoperazone.

The biochemical pattern of the isolate is as follows:

| | | |
|---|---|---|
| Fermentation | Glucose | + |
| Fermentation | Fructose | + |
| Fermentation | Maltose | + |
| Fermentation | Lactose | + |
| Fermentation | Trealose | − |
| Fermentation | Mannitol | − |
| Fermentation | Xylitol | − |
| Fermentation | Melibiose | − |
| Fermentation | Raffinose | − |
| Fermentation | Xylose | − |
| Fermentation | Saccharose | + |
| Production | Nitrates | − |
| Production | Alkaline phosphatase | − |
| Production | Acetoine | − |
| Production | N-acetyl-glucosaminidase | − |
| Production | Arginine hydrolase | + |
| Production | Urease | + |

In many other cases strains showing similar characteristics and adequate to be used for the assay of the invention have been isolated.

EXAMPLE 2

Preparation of the Culture Medium

The culture medium contains the following compounds per 1 liter:

| | |
|---|---|
| $Na_2HPO_4(2H_2O)$ | 10 g |
| $KH_2PO_4$ | 3 g |
| L-aspartic Acid | 150 mg |
| L-alanine | 100 mg |
| L-arginine | 100 mg |
| L-cystine | 50 mg |
| Glycine | 100 mg |
| L-glutammic Acid | 150 mg |
| L-hystidine | 100 mg |
| L-isoleucine | 150 mg |

| | |
|---|---|
| L-lysine | 100 mg |
| L-leucine | 150 mg |
| L-metionine | 100 mg |
| L-phenylalanine | 100 mg |
| L-proline | 150 mg |
| L-serine | 100 mg |
| L-threonine | 150 mg |
| L-triptophane | 100 mg |
| L-tyrosine | 100 mg |
| L-valine | 150 mg |
| Glucose | 10 g |
| $MgSO_4(7H_2O)$ | 500 mg |
| Biotine | 0,1 mg |
| nicotinic Acid | 2 mg |
| D-pantotenic Acid | 2 mg |
| Pyridoxal | 4 mg |
| Pyridoxamine | 4 mg |
| Riboflavin | 2 mg |
| Tiamine | 2 mg |
| Adenine | 20 mg |
| Guanine | 20 mg |
| $CaCl_2(6H_2O)$ | 10 mg |
| $MnSO_4$ | 5 mg |
| $(NH_4)_2SO_4FeSO_4(6H_2O)$ | 6 mg |

The formulation of the medium corresponds to the one described in Hussain, Hastings, White, J. Med. Microbiol. 34:143-147, 1991, with the following modifications, pertaining to the preparation: after all components of the medium are weighed, $MgSO_4(7H_2O)$ is dissolved in distilled water, then all remaining components are added singularly, under continuos shaking. L-cystine prior to addition to the medium must be dissolved in 2-3 drops of 5N NaOH.

Once all components are dissolved (though a small amount of precipitate can persist) the volume is adjusted to 1 l with distilled water and sterilized by filtration through 0.2 µm porous membranes.

EXAMPLE 3

Preparation of the Polysaccharide

Strains are grown in 1000 ml of modified HHW medium for 6 days at 37° C. with shaking.

The bacterial pellet is collected by centrifugation at 13,000×g for 15 minutes at 4° C., suspended in 20 ml of sterile ice-cold physiological saline (NaCl 0.9%), and freezed at −20° C. for 2 h. The bacterial suspension is then thawed at room temperature and homogenized 10 times for 30 seconds with 30 seconds intervals.

The homogenate is then centrifuged at 13,000×g for 15 minutes at 4° C.; the resulting surnatant is stored at 4° C., while the resulting pellet is again suspended in 20 ml of sterile ice-cold saline and homogenized as above described. The surnatant resulting from the second homogenization step is added to the previously obtained one and desalted by dyalisis against 1,000 volumes of distilled water at 4° C. for 2 h, using diylisis membranes with a cut-off of 12 kDa. The sample is then freezed at −80° C., lyophilized, suspended in 5% (W/V) tricloroacetic acid and incubated 15 minutes at 4° C.

The sample is then centrifuged at 30,000×g for 30 minutes at 4° C.; 4 volumes of ice-cold absolute ethanol are then added to the surnatant, that is further incubated at 4° C. for 48 h. The bulk polysaccharide is then collected by centrifugation at 20,000×g for 30 minutes at 4° C., washed with 0.5 volumes of ice-cold absolute ethanol, dehydrated under vacuum and finally suspended in 2 ml of sterile distilled water. The polysaccharide obtained as above described is used to sensitize microtiter wells after adequate dilution (typically in 50 µl aliquots).

EXAMPLE 4

Execution of the ELISA Assay

The wells of a microtiter plate are sensitized with 50 µl of the polysaccharide prepared according to example 3 and diluted 1/80 in sterile distilled water, adequately sealed and incubated 18-24 hours at 4° C. After incubation the wells are emptied and washed 5 times with 100 µl of 0.05% tween 20 in phosphate buffered saline (PBS).

Wells are then emptied, saturated with 200 µl of 10% soy milk in PBS, adequately sealed and incubated at 37° C. for 1 hour. Wells are then emptied, washed as above described, and 50 µl aliquots of the diluted sera are added. Sera, including one positive control and one negative control, are typically diluted 1/160 and 1/320 in PBS. After addition of the sera the wells are adequately sealed and incubated at 37° C. for 1 hour. Wells are then emptied, washed as above described, and 50 µl of either "Peroxidase-Conjugated Rabbit Anti-human IgG" (for example DAKO cod. P0214) (diluted 1/15,000 in 10% soy milk in PBS) or "Peroxidase Conjugated Rabbit anti-Human IgM" (for example DAKO cod. P0215) (diluted 1/1,500 in 10% soy milk in PBS) are added. Wells are then adequately sealed, incubated at 37° C. for 1 hour, emptied and washed as above described.

Following last washing 50 µl of the chromogenic substrate for peroxidase (for example BM Blue POD Substrate Boehringer Mannheim, cod 1484281) are added to each well.

The wells are then incubated 10 minutes at 37° C. and the reaction is then stopped by adding 50 µl of $0.5N\ H_2SO_4$. The $OD_{450\ nm}$ of each well is then evaluated using a microtiter plate reader using one untreated well containing 100 µl of $0.5N\ H_2SO_4$ as the blank.

As a general rule $OD_{450\ nm}$ for positive control should not be over the value 1.5.

Should this happen the assay must be repeated, reducing the time of incubation of the peroxidase substrate.

The invention claimed is:

1. A method for determining the presence of biofilm-forming *staphylococci* adhered to the surface of biomaterials in which at least one *Staphylococcus* strain is involved, said method comprising detecting in blood samples or other biological fluid samples IgM antibodies reacting with a polysaccharide obtained by the following steps:
    (a) culturing a virulent staphylococcal strain deposited with the DSMZ under Accession No. DSM 11942 in modified HHW medium for a period of 4-6 days;
    (b) homogenizing the bacterial cells in a physiological buffer;
    (c) centrifugating at 13,000×g for 15 minutes and separating the supernatant;
    (d) dialyzing the supernatant using a membrane with a cut-off of 12 kDa;
    (e) freezing and lyophilizing the solution obtained in (d);
    (f) suspending the lyophilized material in a deproteinizing solution;

(g) centrifugating at 30,000×g the solution obtained in (f) and separating the supernatant with addition of ethanol;
(h) centrifugating the surnatant of step (g) at 20,000×g to obtain the polysaccharide; and
(i) washing the precipitated polysaccharide with absolute ethanol, dehydrating in vacuo and suspending it in sterile $H_2O$.

2. A method according to claim 1, which the antibodies are reacted with the polysaccharide by ELISA, gel immuno-precipitation, immuno-diffusion, contro-immunoelectrophoresis, radioimmunologic assay or complement fixation.

* * * * *